United States Patent
Chatelain et al.

(10) Patent No.: US 6,825,339 B2
(45) Date of Patent: Nov. 30, 2004

(54) APPARATUS FOR PREPARING POLYNUCLEOTIDES ON A SOLID SUPPORT

(75) Inventors: François Chatelain, Paris (FR); Viktor Kumarev, Villemonble (FR)

(73) Assignee: Proligo, LLC, Boulder, CO (US)

(*) Notice: Subject to any disclaimer, the term of this patent is extended or adjusted under 35 U.S.C. 154(b) by 14 days.

(21) Appl. No.: 10/352,704

(22) Filed: Jan. 28, 2003

(65) Prior Publication Data

US 2003/0176690 A1 Sep. 18, 2003

Related U.S. Application Data

(60) Continuation of application No. 09/119,653, filed on Jul. 21, 1998, now Pat. No. 6,623,703, which is a division of application No. 08/358,556, filed on Dec. 14, 1994, now Pat. No. 5,869,643.

(51) Int. Cl.$^7$ ............................................. C07H 21/00
(52) U.S. Cl. .................. 536/25.3; 536/22.1; 536/25.34; 536/23.1; 536/23.2; 536/25.3; 432/103; 110/345; 435/193; 424/452; 424/464; 424/465; 424/489; 252/182.16; 422/131; 566/25.34
(58) Field of Search ................................ 536/25.3, 22.1, 536/25.34, 23.1, 23.2; 432/103; 110/345; 435/193; 424/452, 464, 465, 489; 252/182.16; 422/131; 566/25.34

(56) References Cited

U.S. PATENT DOCUMENTS 4,192,798 A    3/1980  Verlander et al.

(List continued on next page.)

FOREIGN PATENT DOCUMENTS

| EP | 0 114 599 A1 | 8/1984 |
| EP | 0 130 739 A2 | 1/1985 |
| EP | 0 181 491 A1 | 10/1985 |
| EP | 0 035 719 B1 | 9/1989 |
| EP | 0 375 278 B1 | 6/1990 |
| EP | 0 541 340 A2 | 5/1993 |
| WO | WO 82/03079 | 9/1982 |
| WO | WO 85/01224 | 3/1985 |
| WO | WO 91/17823 | 11/1991 |
| WO | WO 92/02535 | 2/1992 |
| WO | WO 95/01987 | 1/1995 |

OTHER PUBLICATIONS

Pon, "An improved iodine/water oxidation reagent for automated oligonucleotide synthesis," Nucleic Acid Research, vol. 15,, N 17, 7203, 1987.*

Brown, A Brief History of Oligonucleotide Synthesis, *Methods in Molecular Biology, vol. 20: Protocols for Oligonuclotides and Analogs.* S. Agrawal ed., Humana Press, Inc., Totowa, NJ (1993).

Karger, Barry et al., An Introduction to Separation Science, "A Wiley–Interscience Publication" (1973) pp. 124 and 288.

*Primary Examiner*—Elli Peselev
*Assistant Examiner*—Devesh Khare
(74) *Attorney, Agent, or Firm*—Swanson & Bratschun, L.L.C.

(57) ABSTRACT

The present invention relates to an apparatus for preparing polynucleotides on a solid support in a reactor comprising a column containing an immobilized solid support that is functionalized for polynucleotide synthesis. The solid support can be porous, and can be functionalized with a nucleoside or with a universal synthesis of polynucleotides.

3 Claims, 2 Drawing Sheets

DIAGRAM OF THE LARGESCALE SYNTHESIZER

U.S. PATENT DOCUMENTS

| | | |
|---|---|---|
| 4,353,989 A | 10/1982 | Bender et al. |
| 4,362,699 A | 12/1982 | Verlander et al. |
| 4,373,071 A | 2/1983 | Itakura et al. |
| 4,458,066 A | 7/1984 | Caruthers et al. |
| 4,517,338 A | 5/1985 | Urdea et al. |
| 4,659,774 A | 4/1987 | Webb et al. |
| 4,689,405 A | 8/1987 | Frank et al. |
| 4,698,208 A | 10/1987 | Patchornik et al. |
| 4,746,490 A | 5/1988 | Saneii |
| 4,908,405 A | 3/1990 | Bayer et al. |
| 4,959,463 A * | 9/1990 | Froehler et al. ........... 536/25.3 |
| 5,047,524 A | 9/1991 | Andrus et al. |
| 5,223,435 A | 6/1993 | Kohr |
| 5,241,998 A | 9/1993 | Ashraf-Khorassani |
| 5,252,296 A | 10/1993 | Zuckermann et al. |
| 5,262,530 A | 11/1993 | Andrus et al. |
| 5,298,259 A | 3/1994 | Lloyd et al. |
| 5,869,463 A | 2/1999 | Major et al. |
| 5,869,643 A * | 2/1999 | Chatelain et al. .......... 536/25.3 |
| 6,469,157 B1 * | 10/2002 | Chatelain et al. .......... 536/25.3 |

\* cited by examiner

APPARATUS FOR PREPARING POLYNUCLEOTIDES ON A SOLID SUPPORT

This application is a continuation of U.S. Ser. No. 09/119,653, filed Jul. 21, 1998 now U.S. Pat. No. 6,623,703, which is a divisional of U.S. Ser. No. 08/358,556, filed Dec. 14, 1994, now U.S. Pat. No. 5,869,643, which claims the benefit of priority of French application no. FR 93 15164, filed Dec. 16, 1993, now abandoned. Each of the foregoing applications/patents are incorporated herein in their entirety by reference.

FIELD OF THE INVENTION

The present invention relates to a process for preparing polynucleotides on a solid support. The present invention also relates to a reactor containing a solid support and to a device including this reactor, which are useful in the process for preparing polynucleotides according to the invention.

BACKGROUND OF THE INVENTION

The synthesis of polynucleotides on a solid support is particularly used in automated syntheses of DNA or RNA oligonucleotides. In the present application, "polynucleotides" is understood to mean deoxyribonucleic acid or ribonucleic acid fragments or, more generally, polynucleotides or oligonucleotides where the bases, internucleotide phosphate linkages, or alternatively the ribose rings of the bases, can be chemically modified in a known manner. This may be especially oligonucleotides with α or β anomers, oligonucleotides with inter-nucleotide linkage of the phosphorothioate or methyl phosphonate type, or alternatively oligothionucleotides.

The principle for the chemical synthesis of nucleic acids on a solid support is nowadays widely described in the specialist literature, and a number of apparatus are available on the market which perform automatically all or part of the synthesis steps. Among the chemical routes described, only the so-called phosphoramidites method (Caruthers et al.: EP 0,035,719 BI) is up until now sufficiently efficient to envisage the production of nucleic acids on an industrial scale.

The preparation of oligonucleotides or polynucleotides is carried out in a reactor containing a solid support and comprises the treatment of the solid support such as an inorganic polymeric support by a series of successive steps, each of the series leading to the addition of a new nucleotide on the support. The series of successive steps, or synthesis cycles, are carried out as many times as is required by the manufacture of an oligonucleotide or a polynucleotide of desired length.

In a process for synthesizing polynucleotides on a solid support, the solid support traditionally consists of glass beads of controlled porosity (CPG) or, more generally, of particles of a functionalized inorganic or organic polymer.

The techniques conventionally used involve the use of eight different reagents as solid supports, consisting of the said functionalized inorganic or organic polymer linked to a nucleoside A, T, C, G or U, depending on whether the sequence to be prepared contains, as first deoxyribo- or ribonucleotide A, T, C, G or U. Manufacturers therefore supply reactors in which one of these nucleosides has previously been attached to the support. Depending on whether the sequence starts with A, T, C, G or U, the appropriate reactor is then chosen. The elongation of this first nucleoside then occurs in the 3'→5', or 5'→3' direction, using coupling reagents.

Numerous supports have already been described in the literature for the solid phase synthesis of oligonucleotides. There may be mentioned organic polymers such as polystyrene (Nucleic Ac.1980, volume 8), polyacrylamide acryloylmorpholide, polydimethylacrylamide polymerized on kieselguhr (Nucleic Ac. 9(7):691 (1980)).

Other supports described are of inorganic nature, in particular based on silica functionalized by a hydrocarbon radical carrying an $NH_2$ and/or COOH group (J. Am. Chem., 105:61 (1983)), or the support based on silica functionalized by a 3-aminopropyltriethoxysilane group whose use in phosphite and phosporamidite synthesis for the preparation of oligonucleotides was described for the first time in European Patent No. 0,035,719.

There is known, from French Patent Application FR 93 08 498 and PCT/FR94/00842, a process for the solid phase synthesis of oligonucleotides in which a so-called "universal" support is used, that is to say a solid support which can be used regardless of the first nucleotide of the RNA or DNA to be synthesized, regardless of the type of monomeric reagent used during the synthesis, that is to say regardless of the type of substitution on the phosphate group in 3' or in 5', depending on whether the synthesis is carried out in the 5'→3' or 3'→5' direction.

In particular, the "universal nature" of the solid phase supports can be obtained by functionalization of the inorganic or organic polymer with a hydrocarbon radical containing glycol type groups in which an OH group and a nucleophilic group are present in the vicinal position, that is to say on two adjacent carbons, at the end of the hydrocarbon radical, it being possible for these two carbons to be optionally substituted by inert groups. "Inert group" is understood here to mean a group which does not react under the conditions encountered during the various steps of the synthesis on a solid support of nucleic acids according to the invention.

In a specific embodiment, a process for synthesizing polynucleotides comprises the following steps of:

1) condensing the OH group in 5' or 3' of the first nucleotide or of an oligonucleotide linked at its other 3' or 5' end to the said solid support, by means of a coupling agent, with the phosphate group optionally substituted respectively in position 3' or 5' of a monomeric nucleotide reagent protected in 3' and 5';

2) oxidizing or sulfurizing the phosphite type internucleotide linkage obtained in step 1) into a phosphate linkage respectively;

3) deprotecting the 5'-O or 3'-O end of the product obtained in step 2);

4) repeating steps 1) to 3) as many times as there are nucleotides to be added in order to synthesize the nucleic acid.

The above steps lead to an oligonucleotides linked to the solid support. The process comprises a final step of detaching the nucleic acid from the support and removing the groups for protecting the bases and, where appropriate, the 2'-O positions of the nucleic acid.

In the techniques where the solid support is already linked to a first nucleoside corresponding to the first nucleotide of the sequence to be prepared, before the start of the synthesis cycles, the said support generally contains a protection in 5' or 3' of the said nucleoside. In this case, the synthesis cycle starts with a deprotection step in acidic medium, in general a detritylation.

According to the variants used most commonly, the said monomeric nucleotide reagent corresponds to the formula:

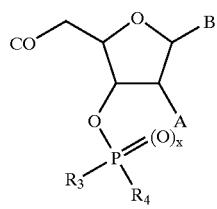

in which:

A represents H or an optionally protected hydroxyl group, is a purine or pyrimidine base whose exocyclic amine functional group is optionally protected, C is a conventional protective group for the 5'-OH functional group, x=0 or 1 with a) when x=1:

$R_3$ represents H and $R_4$ represents a negatively charged oxygen atom, or $R_3$ is an oxygen atom and $R_4$ represents either an oxygen atom or an oxygen atom carrying a protecting group, and b) when x=0, $R_3$ is an oxygen atom carrying a protecting group and $R_4$ is either a hydrogen or a disubstituted amine group, when x is equal to 1, $R_3$ is an oxygen atom and $R_4$ is an oxygen atom, the method is in this case the so-called phosphodiester method; when $R_4$ is an oxygen atom carrying a protecting group, the method is in this case the so-called phosphotriester method, when x is equal to 1, $R_3$ is a hydrogen atom and 4 is a hydrogen atom and $R_4$ is a negatively charged oxygen atom, the method is in this case the so-called H-phosphonate method, and when x is equal to 0, $R_3$ is an oxygen atom carrying a protecting group and $R_4$ is either a halogen, the method is in this case the so-called phosphite method and, when $R_4$ is a leaving group of the disubstituted amine type, the method is in this case the so-called phosphoramidite method.

The steps of a cycle of synthesis by the phosphoramidite method are conventionally the following:

1) condensation of the 5' terminal hydroxyl of a nucleoside or of an oligonucleotide covalently attached to the solid support with a phosphite type compound according to the reaction:

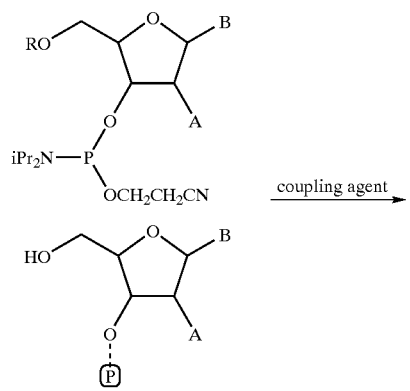

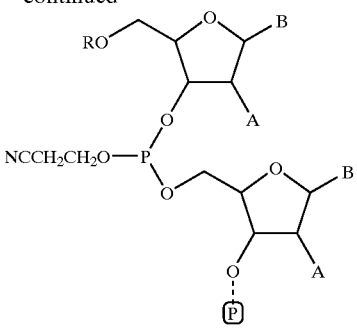

2) oxidation of the phosphite bond obtained to a phosphate according to the reaction:

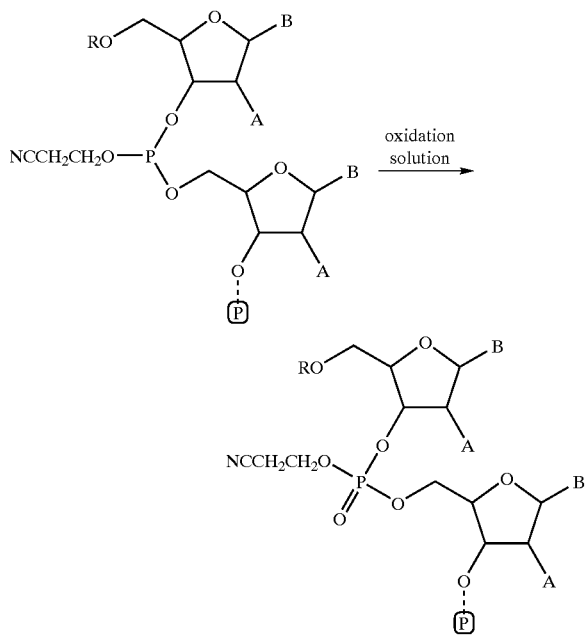

3) blocking of the hydroxyl groups of the unreacted nucleosides;
4) liberation of the 5' terminal hydroxyl from the last nucleoside so as to generate an active site for the next synthesis cycle.

Each nucleotide is sequentially added to the support by repeating steps 1 to 4. At the end of the synthesis, the oligonucleotide is separated from the support and freed of its protecting groups by a controlled hydrolysis reaction.

Commercial synthesizers specialized in the synthesis of oligonucleotides are designed so as to automatically carry out the synthesis steps described above. These synthesizers are generally composed of a reactor containing the solid support, a reagent mixer, one or several unit(s) for selecting the reagents and the vessels containing the said reagents. The synthesis steps are carried out by successively adding the selected reagents to the reactor. Most often, the solid support is washed with acetonitrile after each step.

The solid support is not immobilized and does not occupy the whole volume of the reactor but, in general, only half of the volume of the reactor, and in any case no more than three quarters, so as to allow adequate stirring of the solid phase.

The reactor, as used in commercial synthesizers, has the shape of a vessel crossed by the flow of reagents which causes the stirring (or fluidization) of the solid support. It is indeed considered that the stirring of the solid phase is essential because it allows better penetration of the solvents and reagents into the pores of the solid phase generally consisting of porous beads or porous membranes (see Methods in Molecular Biology: Protocols for Oligonucleotides and Analogs—Synthesis and Properties—Edited by Sudhir Agrawal—1993—Humana Press; Totowa, N.J., pages 442–444 and 454).

The mixer is situated upstream of the reactor, connected to it by a pipeline. The units for selecting the reagents generally consist of electrovalves and allow selective opening of the inlets/outlets of the hydraulic circuit as well as the routes for the passage of the reagents. The cohesion of the hydraulic system is ensured by a series of suitably connected tubes or capillaries. It is recommended to install the equipment in an air-conditioned room at 20° C., the temperature at which the reactions are performed.

While the efficiency of the reactions is sufficient under these conditions, the duration of the reactions and the required excess of reagents in order to carry out good washing by successive dilutions are the principal disadvantages of the synthesizers as described above. In this case, the consumption of reagents and the duration of the syntheses are substantially greater than the values calculated on the basis of known laws of organic synthesis. These disadvantages were attributed to the limiting factor which the rate of diffusion of the reagents in the pores constitutes.

SUMMARY OF THE INVENTION

The aim of the invention is the improvement of the efficiencies of existing methods of synthesis of oligonucleotides.

The method according to the present invention consists in a modification of organic synthesis apparatuses and parameters so as to improve the productivity thereof. The improvements affect in particular the duration and the consumption of reagents necessary for carrying out a synthesis.

The subject of the present invention is also a reactor for preparing polynucleotides according to a process of the invention, the reactor being in the form of a column containing a solid support through which the solutions of reagents and/or solvents are circulated, wherein the solid phase constituting the solid support is immobilized in said reactor such that said solutions migrate in the column and through said solid phase according to a frontal progression, the successive solutions of each step of a synthesis cycle not mixing at all or very little.

In particular, the subject of the present invention is therefore a reactor which is useful in a process for preparing polynucleotides on a solid support, which consists of a cylindrical column completely filled with particles of porous materials constituting a solid support as described above.

The subject of the present invention is finally a device for the synthesis of polynucleotides on a solid support containing a thermostatted reactor and a thermostatted collector which performs the collection, the heating to the temperature of the reactor, then the mixing of the reagents before their introduction into the reactor.

Other advantages and characteristics of the present invention will appear in the light of the detailed description below.

DETAILED DESCRIPTION OF THE INVENTION

Figure 1:
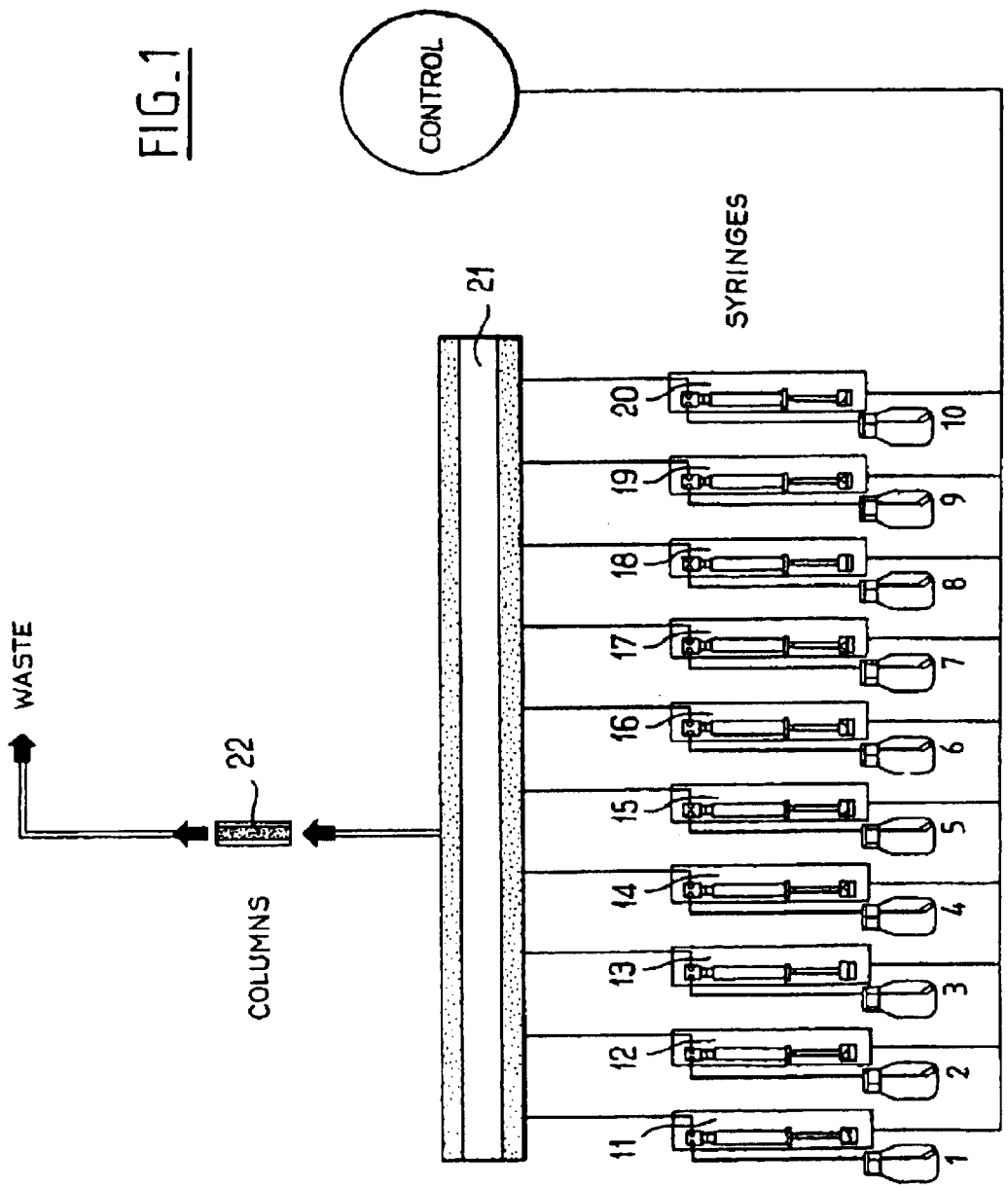
FIG. 1 illustrates a "LargeScale Synthesizer" of the invention.

It was discovered according to the present invention that it is mainly the geometry of the vessel-type reactor in which the free particles of the solid support are stirred according to the principle of "pseudoliquid" phase reaction which has numerous disadvantages.

It was also discovered that several other parameters are also called into question which considerably reduce the productivity of the synthesizers:
  the reagents used for the oxidation step (iodine solution, tetrahydrofuran, lutidine, water) are degraded over time, and the resulting reduction in reactivity rapidly induces a reduction in the efficiency of the synthesis;
  the absence of thermostatting of the reactor and of the reagents leads to the loss of reproducibility of the syntheses.

The hydraulic system itself often comprises unusable dead volumes. The time spent by the reagents in these dead volumes and in the mixing chamber, in particular during the activation of phosphoramidite by the coupling agent, limits the reactivity of the transient species formed.

Accordingly, the present invention relates to a set of modifications made to the system described above which has the effect of improving the productivity by reducing the consumption of reagents and the durations of synthesis.

The essential characteristic of the process according to the present invention relates to the immobilization of the solid phase or to the method of filling the reactor with the solid phase.

The subject of the present invention is indeed a process for preparing polynucleotides on a solid support in a reactor in the form of a column through which solutions of reagents and/or solvents are circulated, wherein the solid phase constituting said solid support is immobilized in said reactor, and said solutions migrate in the column and through the solid phase according to a frontal progression, such that the successive solutions from each step of a synthesis cycle do not mix.

The subject of the present invention is also a process for preparing polynucleotides on a solid support in a reactor in the form of a column through which the solutions of reagents and/or solvents are circulated, wherein the reactor is a column completely filled with particles of a porous material constituting said solid support.

In this embodiment where the solid support consists of free particles of a porous material filling a column, the particles are also immobilized. The immobilization indeed results from the fact that by "completely filled column" there is understood here that the degree of filling with particles and the density of distribution of the particles in the column are such that the particles are sufficiently packed such that they can no longer move when a liquid crosses the column.

It may be only a portion of the column which is completely filled provided that the particles of the solid support are maintained by appropriate means in said portion of the column.

In an advantageous embodiment, the column will have a cylindrical shape. It is thus proposed, for the first time, to use a "chromatography column" type reactor, that is to say a column consisting of a cylindrical tube completely filled with the solid phase.

This type of column, homogeneously filled with the solid support, offers several advantages: the various solutions which follow each other in the reactor do not mix, or very little, there is therefore no phenomenon of dilution of the solutions by the previous reagent and the washing following each step of the synthesis cycle is thereby greatly facilitated. According to the chromatography column principle, the successive solutions introduced at one end of the column migrate according to a frontal progression, such that a solution "pushes" the preceding one.

It was indeed observed that the solid phases conventionally used in solid phase oligonucleotides synthesis are such that the affinity and the physicochemical interactions of the various reagents and solvents used are negligible and do not interfere with their diffusion through the solid phase other than by the desired chemical reactions.

It should be mentioned that, of course, in the interface region between the solutions, slight mixing may occur locally between the solutions when the circulation rates of the solutions are high. However, this mixing, which is localized at the interface, is in no way comparable with what is observed in prior processes for which the washes were based on the principle of dilution by mixing successive solutions.

Contrary to the conventional model, these reactors therefore make it possible to substantially reduce the volumes of reagents required. The useful flow rates are adjusted as a function of the diffusion constants and the kinetics of the reactions called into play. The duration of the synthesis cycles is thereby considerably reduced. For each type of particle, depending on its porosity, the flow rate of the reagents through the column should not exceed a certain value above which the reagents no longer diffuse inside the pores. This is a well known phenomenon in chromatography.

In addition, within the reactor and regardless of its size, the conditions are locally always identical. The system can therefore be applied to all scales of synthesis.

In particular, there may be mentioned materials consisting of inorganic polymers, especially glass, silica, metal oxides, or of organic polymers, especially cellulose, or optionally substituted polystyrene.

Preferably, the polymer is an inorganic polymer prepared based on glass or silica, especially a silica gel.

The said particles may consist of microbeads or agglomerated microfibers.

Preferably, in the reactor according to the present invention, there may be used as particles of the solid support porous microbeads, thereby providing the largest functionalized surface area in terms of weight of nucleosides linked to the polymer per weight of polymers. The size of the beads may range from 5 $\mu$m to 500 $\mu$m, more generally from 40 $\mu$m to 70 $\mu$m. The pores may optionally pass right through the microbeads. The diameter of the pores may range between 200 Å and 10,000 Å. Two pore sizes may be used, with wide pores (about 10,000 Å) and smaller pores (300 Å). This type of pore of variable size favors the diffusion of the solutions through the solid phase.

The reactor according to the present invention makes it possible to best exploit known laws of diffusion and kinetics of bimolecular chemical reactions according to which the reagents in solution diffuse very rapidly into the pores of the solid support and the kinetics of condensation of the free nucleoside with the 5'OH end of the oligonucleotides attached to the support is practically instantaneous.

The regulation of the temperature of the reactor and the reagents is another essential characteristic of the present invention which, so far, does not exist in any synthesizer on the market.

The working temperature is one of the parameters which directly and simultaneously influence the kinetics of the chemical reactions called into play, but also the stability of the reagents and the viscosity of the solutions. Contrary to all the prejudice which claims that the synthesis of the oligonucleotides decreases the efficiency above 30° C., it is recommended according to the present invention to thermostat the reactor at an optimal temperature of 45° C. The regulation of the temperature of the system makes it possible to act on the kinetics of the chemical reactions called into play as well as on the viscosity of the solutions used.

Advantageously, the reagents, that is to say the coupling reagents such as tetrazole, and the monomeric reagents, on the one hand, and/or the various reagents of the oxidizing solution, on the other hand, are mixed immediately upstream of the reactor, or optionally, just upstream of a system of distribution of the reagents in a multicolumn system. The unusable dead volumes are thereby reduced.

In particular, the reagents are heated before introducing them into the reactor and, where appropriate, before mixing them.

Indeed, if the reagents are heated only after mixing them, a mutual inactivation and a loss of reactivity on the column are observed. More precisely, early mixing (too far from the reactor) of the reagents can lead to undesirable side reactions. In particular, the mixing of the tetrazole (weak acid) and the phosphoramidites can result in the detritylation of part of the monomers. The phosphoramidites can then react with each other. This type of reaction leads to the formation of homopolymers which may or may not react with the oligonucleotide attached to the support. The formation of oligonucleotides which are longer than desired can be observed in this case. Whatever the case, the synthesis yield is always thereby reduced. Of course, these phenomena are accentuated by heating. It is therefore advisable to heat the reagents before mixing them.

In the reactors used before the present invention, above 30° C., the reagents become rapidly degraded. But, by means of the reactor according to the present invention, which favors the kinetics of the reactions, it is possible to increase the temperature up to 90° C. (between 20 and 90° C.), preferably the temperature of the reactor is adjusted between 30 and 60° C., especially to 45° C.

Advantageously, the deprotection step in acidic medium is performed with TFA (trifluoroacetic acid) in dichloromethane. A 1% v/v solution of trifluoroacetic acid in extra dry dichloroethane is especially used during the step for liberation of the terminal 5' hydroxyl functional group (step 4) by replacing the standard solution (2% dichloroacetic acid in dichloromethane). This recommendation makes it possible in particular to get rid of the possible phenomena of boiling of dichloromethane when the working temperature exceeds 40° C.

The mixing of acetic acid and pyridine causes an increase in the temperatures from 40° to 60° C., which facilitates the maintenance of the temperature at said temperatures.

By virtue of the very high coupling yields (probably greater than 99%) of the process according to the invention, the step of blocking (or "capping") the unreacted 5'-OH functional groups (step 3) proves, in most cases, not to be very efficient, or even completely pointless and can therefore be omitted. Thus, no accumulation of synthetic fragments of size n-1 is observed as would be expected if no capping step is performed. Probably, when the efficiency of the reactions is optimal, the unreacted species are permanently inaccessible.

According to another characteristic of the present invention, the oxidation step is performed with iodine in acetic acid and pyridine. Thus, in place of the conventional oxidation solution, two reagents are used separately, one consisting for example of an iodine solution saturated with glacial acetic acid, the other being ultrapure pyridine. These reagents are advantageous in that, at the oxidation step (step 2 above), these two solutions can be mixed in stoichiometric quantities at the inlet of the reactor. The mixture thus formed is injected into the reactor and instantaneously and quantitatively ensures the oxidation of the newly formed internucleotide bond. Thus, advantage is taken of the stability of the two separate solutions by indefinitely guaranteeing the reproducibility of the oxidation step.

Two oligonucleotides or polynucleotide synthesizers, designed on the basis of the technical improvements described above, were produced. The performances and the productivity of these two apparatus are thereby substantially increased compared to apparatus on the market.

The first synthesizer was designed to synthesize quantities of oligonucleotides between 50 µmol and 1 mmol. These performances can therefore be compared to those of commercial synthesizers which are present on the market and are capable of working at equivalent synthesis scales. This apparatus is called "LargeScale Synthesizer". It is represented in FIG. 1.

Figure 2:
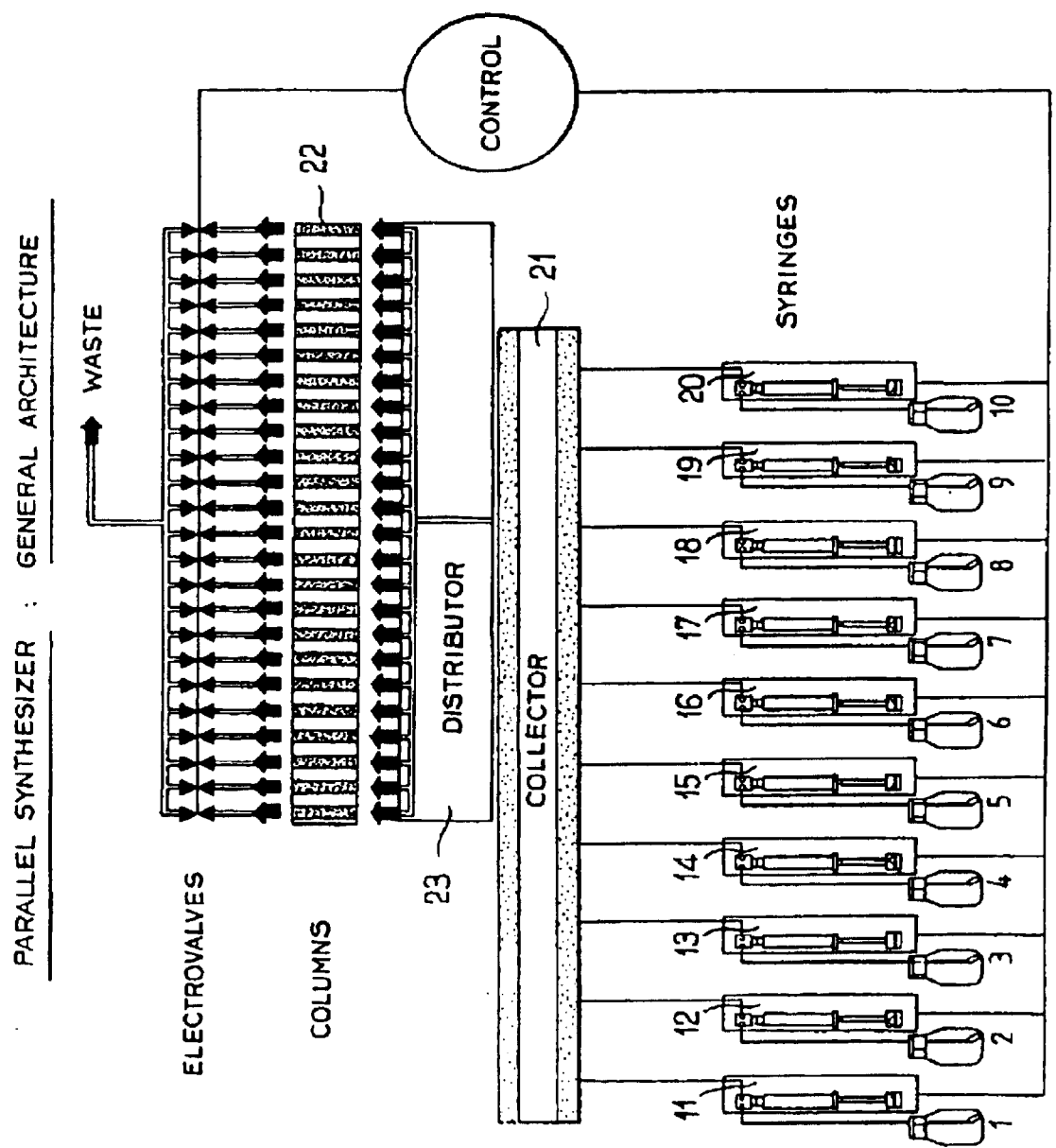
FIG. 2 illustrates a "Multicolumn Synthesizer" of the invention.

The function of the second apparatus is to synthesize, in parallel, 24 different oligonucleotides or polynucleotides. The scale of each synthesis is between 0.05 and 1 µmol. So far, this apparatus has no equivalent. Its productivity can be compared to that of 6 synthesizers—4 columns on the market. It is called "Multicolumn Synthesizer". It is represented in FIG. 2.

These two apparatus comprise:
the vessels [(1) to (10)] containing the reagents, each comprising a syringe type positive displacement pumping module [(11) to (20)];
a thermostatted collector [(21)] whose attributes are the collection, the heating and the regulation of the temperature and the mixing of the moving reagents.

The "LargeScale Synthesizer" is equipped with a "filled column" type reactor whose dimensions are adjusted as a function of the desired synthesis scale [(22)].

The "Multicolumn Synthesizer" is equipped with 24 microcolumns [(22)] of the same type as the "Large-Scale Synthesizer" but whose dimensions make it possible to work at the scales 0.05 µmol, 0.1 µmol, 0.2 µmol and 1 µmol. Between the collector and the reactors is a distributor [(23)] responsible for equally distributing the reagents between the 24 columns.

Finally, a block composed of 24 electrovalves, individually controlled at each column, makes it possible to select, at each synthesis step, the reactors "in service".

The volumes, the flow rates and the waiting times are under the control of a computer. The program controls the correct sequence and the execution of the cycles in conformity with the sequences to be synthesized.

In order to guarantee local conditions which are always identical regardless of the number -of reactors in service, the "Multicolumn Synthesizer" functions according to an interactive mode. Thus, the volumes and the flow rates of each of the reagents are adjusted, at each instant, to the number of syntheses in progress.

A—Course of a Synthesis with Phosphoramidite in the LargeScale Synthesizer

The synthesis scale is chosen at the time the program is initiated.

Each synthesis starts with an initialization cycle which makes it possible to wash and thermostat the reactor to the working temperature.

The program comprises five synthesis cycles corresponding to each of the four bases and to the possible modified bases.

The synthesis cycles can be broken down into synthesis steps or procedures which follow one another in the following chronological order:

1) Detritylation: liberation of the hydroxyl in position 5' of the nucleoside or of the oligonucleotide covalently attached to the solid support,
2) First washing;
3) Addition of the base: condensation of the phosphoramidite type monomer with the free 5' terminal hydroxyl of the nucleoside or of the oligonucleotide attached to the solid support. Formation of internucleotide bond;
4) Second washing;
5) Oxidation of the previously formed phosphite type internucleotide bond into phosphate;
6) Third washing.

These cycles are repeated as many times as is required by the oligonucleotide synthesis or the synthesis of a polynucleotide of desired length.

B—Course of a Synthesis in the Multicolumn Synthesizer

The synthesis scale is chosen at the time the program is initiated.

Each synthesis starts with an initialization cycle which makes it possible to wash and thermostat the reactors to the working temperature.

There is only one synthesis cycle which is repeated as many times as is required by the manufacture of the 24 oligo- or polynucleotides.

The cycle can be broken down in the following manner:

a) selection of the columns to be detritylated.
1) Detritylation: liberation of the hydroxyl in position 5' of the nucleoside or of the oligonucleotide covalently attached to the solid support.
2) First washing:
b1) Selection of the columns which should receive the A base.
3-1) Addition of the A base: condensation of the phosphoramidite type A monomer with the free 5' terminal hydroxyl nucleoside or of the oligonucleotide attached to the solid support. Formation of the internucleotide bond.
b2) Selection of the columns which should receive the G base.
3-2) Addition of the G base: condensation of the phosphoramidite type G monomer with the free 5' terminal hydroxyl of the nucleoside or of the oligonucleotide attached to the solid support. Formation of the internucleotide bond.
b3) Selection of the columns which should receive the T base.
3—3) Addition of the T base: condensation of the phosphoramidite type T monomer with the free 5' terminal hydroxyl of the nucleoside or of the oligonucleotide attached to the solid support. Formation of the internucleotide bond.

b-4) Selection of the columns which should receive the C base.
   3-4) Addition of the C base: condensation of the phosphoramidite type C monomer with the free 5' terminal hydroxyl of the nucleoside or of the oligonucleotide attached to the solid support. Formation of the internucleotide bond.
c) Selection of the oxidizing columns.
   4) Second washing.
   5) Oxidation of the previously formed phosphite type internucleotide bond into phosphate.
   6) Third washing.

DESCRIPTION OF THE STEPS MENTIONED ABOVE

Each step can be described with reference to the diagrams provided for the synthesizers (FIGS. 1 and 2).

1) Detritylation: reagent no. 10, preferably a 1% v/v solution of trifluoroacetic acid in extra dry dichloroethane, is pushed through the reactor by means of the syringe module no. 10.
   The volume necessary is between 2 and 10 times the volume of the empty reactor.
   The flow rate in the column is less than 500 cm/min. This flow rate unit in cm/min in fact represents the linear speed of the solutions inside the column and is therefore independent of the diameter of the column. The volume flow rates should be adjusted as a function of the diameter of the reactor. In order to change the size of the reactor while locally preserving the synthesis conditions, it is sufficient to modify the volume flow rate while ensuring that the linear speed inside the reactor, given in cm/min, does not change.
   The flow rates which are used are compatible with the diffusion constants in the pores, that is to say that the linear speed of the solutions inside a column is not greater than the speed of diffusion through the pores. In the opposite case, there would be a low efficiency of the reagents and of the washes resulting in a decrease in the synthesis yields.
   The total reaction time is between 10 and 120 seconds.

2) First washing: the reagent no. 1, preferably extra dry acetonitrile, is pushed through the reactor by means of the syringe module no. 1.
   The volume required is between 2 and 10 times the volume of the empty reactor.
   The flow rate in the column is less than 500 cm/min.

3) Coupling: the reagents no. 3, or no. 4, or no. 5 or no. 6, or no. 7, and no. 2, respectively a 0.1 M solution of each monomer and a 0.45% solution of tetrazole in acetonitrile, are conjointly pushed through the reactor by means of the syringe modules no. 3, or no. 4, or no. 5, or no. 6, or no. 7, and no. 2 respectively.
   The ratios of the volumes and the flow rates of the reagents no. 3, or no. 4, or no. 5, or no. 6, or no. 7, and no. 2 may be different from 1.
   The total volume required is between 2 and 10 times the volume of the empty reactor.
   The overall flow rate in the column is less than 500 cm/min.
   The reaction time is less than 1 minute.

4) Second washing: the reagent no. 1, preferably extra dry acetonitrile, is pushed through the reactor by means of the syringe module no. 1.
   The volume required is between 0.5 and 5 times the volume of the empty reactor.
   The flow rate in the column is less than 500 cm/min.

5) Oxidation: the reagents no. 8 and no. 9, respectively a saturated solution of iodine in glacial acetic acid and ultrapure pyridine, are conjointly pushed through the reactor by means of the syringe modules no. 8 and no. 9 respectively.
   The ratios of the volumes and flow rates of the reagents no. 8 and no. 9 are equal to 1.
   The total volume required is between 1 and 5 times the volume of the empty reactor.
   The overall flow rate in the column is less than 500 cm/min.
   The reaction time is less than 30 seconds.

6) Third washing: the reagent no. 1, preferably extra dry acetonitrile, is pushed through the reactor by means of the syringe module no. 1.
   The volume required is between 1 and 5 times the volume of the empty reactor.
   The flow rate in the column is less than 500 cm/min.

The following exemplary embodiment sizes serve to illustrate the process according to the invention.

EXAMPLES

Example 1

Synthesis of an Oligonucleotide, at the 30 µmol scale, with the aid of the LargeScale Synthesizer The apparatus used is that previously described.

The reactor used is a cylindrical glass column, of diameter 10 mm and height 25 mm.

The working temperature is 45° C.

The synthesis cycles are detailed in Table 1.

An oligodeoxynucleotide, 18 bases long, whose sequence is: d(ACG TTC CTC CTG CGG GAA) is synthesized under these conditions.

The reactor is carefully filled with 0.66 g of CPG 500 Å (CPG INC., USA), "derivatized" by the first A nucleoside. The capacity of the support is 45 µmol/g (density of 3 ml/g).

The synthesis scale is 30 µmol.

After a step of washing with acetonitrile, the synthesis cycle as described in Table 1 is performed 17 times.

Under these conditions, the oligonucleotide, of the desired length, retains the transient dimethoxytrityl group at the 5' terminal position.

The oligonucleotide is separated from the CPG and liberated from the permanent protecting groups by an appropriate treatment of the support, "derivatized" according to the method described above, with 10 ml of a 30% aqueous solution of ammonium hydroxide, for 16 hours at 55° C.

After adding 40 ml of absolute ethanol and 1 ml of a 3M aqueous solution of sodium acetate, the oligonucleotide is left to precipitate for two hours at 0° C.

The precipitate is then filtered on a 1.2 µ lopridyne membrane (PALL S.A., FRANCE) and resolubilized in 10 ml of water.

After reading the optical density at 260 mm, 4000 O.D.U., that is to say 120 mg of crude synthesis mixture, are obtained.

The purity of the oligonucleotide of the desired length, estimated by HPLC on a reversed-phase column, is 88%.

Example 2

Synthesis of an Oligonucleotide, at the 77 µmol Scale with the Aid of the LargeScale Synthesizer The apparatus used is the same as for the preceding example.

The reactor used is a cylindrical glass column, of diameter 10 mm and height 25 mm.

The working temperature is 45° C.

The synthesis cycles are detailed in Table 2.

An oligodeoxynucleotide, 18 base in length, whose sequence is: d(TTC CGC CAG GAG GAA CGT) was synthesized under these conditions.

The reactor is carefully filled with 0.66 g of High-Loaded CPG 500 Å, "derivatized" by the first T nucleoside. The capacity of the support is 110 µmol/g, its density 3 ml/g (MILLIPORE S.A., FRANCE).

The synthesis scale is 77 µmol.

After a step of washing with acetonitrile, we performed the synthesis cycle as described in Table 2 17 times.

Under these conditions, the oligonucleotide, of the desired length, retains the transient dimethoxytrityl group at the 5' terminal position.

The conditions for deprotection and recovery of the oligonucleotide are the same as those described in the preceding example.

After reading the optical density at 260 nm, 8,500 O.D.U., that is to say 255 mg of crude synthesis mixture, are obtained.

The purity of the oligonucleotides of the third length, estimated by HPLC on a reversed-phase column, is 84%.

Example 3

Synthesis of an Oligonucleotide, at the 100 µmol Scale, with the Aid of the LargeScale Synthesizer The apparatus used is the same as for the previous example.

The reactor used is a cylindrical glass column, of diameter 15 mm and height 34 mm.

The working temperature is 45° C.

The synthesis cycles are detailed in Table 3.

An oligonucleotide, 56 bases in length, whose sequence is d(TAA CCA CAC TTT TTG TGT GGT TAA TGA TCT ACA GTT ATT TTT TAA CTG TAG ATC AT) is synthesized under these conditions.

The reactor is carefully filled with 2 g of CPG 500 Å, "derivatized" by the first T nucleoside. The capacity of the support is 50 µmol/g, its density 3 ml/g (MILLIPORE S.A., FRANCE).

The synthesis scale is 100 µmol. After a step of washing with acetonitrile, we performed the synthesis cycle as is described in Table 3 55 times.

Under these conditions, the oligonucleotide, of the desired length, retains the transient dimethoxytrityl group at the 5' terminal position.

The conditions for deprotection and recovery of the oligonucleotide are the same as those described in the previous examples.

After reading the optical density at 260 nm, 31,000 O.D.U., that is to say 930 mg of crude synthesis mixture, are obtained.

The purity of the oligonucleotide of length 56 mers, estimated by HPLC on a reversed-phase column, is 61%.

Example 4

Simultaneous Syntheses of 24 Different Oligonucleotides with the Aid of the Multicolumn Synthesizer The reactors are metallic micro columns of diameter 1.5 mm and height 6 mm.

The working temperature is 50° C.

The synthesis cycles are detailed in Table 4.

We synthesized, under these conditions, the oligodeoxynucleotides whose sequences are given in Table 5.

The reactors are evenly filled with 2 mg of universal CPG 500 Å containing an epoxide group (prepared according to Example 1 of patent application FR 93 08 498). The capacity of the support is 50 µmol/g (GENSET S.A., FRANCE) (density: 3 ml/g).

The synthesis scale is 0.1 µmol.

After a step of washing with acetonitrile, we performed the operations described in Table 4 as many times as is required by the synthesis of the 24 oligodeoxynucleotides of Table 5.

The conditions for deprotection and recovery of the oligonucleotide are the same as those described in the preceding examples.

After reading the optical density at 260 nm, 11 O.D.U. are obtained on average from each of the oligonucleotides, that is to say 0.33 mg. The purity of the oligonucleotides, estimated by HPLC, on a reversed-phase column for the 5' O-Trityl oligodeoxynucleotides, and on an anion exchange column for the 5'OH oligonucleotides, exceeds 84%.

Comparative Example 5

Table 6 below presents the characteristics of the syntheses carried out with fluidized bed reactors marketed by APPLIED BIOSYSTEMS and MILLIPORE as described in the literature.

The synthesizers used are the following:

APPLIED SYNTHESIZER, model 394:
reactor in the form of a column:
diameter 5 mm
height 6 mm
volume 0.11 ml
Solid support: CPG 500 Å (CPG INC., USA)
  capacity: 30 µmol/g
  density: 3 ml/g
For a synthesis at the 0.2 µmol scale:
  6.7 mg of CPG, that is to say a volume of 0.02 ml and a degree
  of filling of 20%.
MILLIPORE SYNTHESIZER, model 8800:
Reactor in the form of a 225 ml vessel which can be used with 1 to 15 g of synthesis of CPG.
For our examples:
"STANDARD" method for 100 µmol
solid support: CPG 500 Å (MILLIPORE S.A., FRANCE)
  capacity: 30 µmol/g
  density: 3 ml/g
For 100 µmol: 3.33 g of CPG that is to say 10 ml of phase and a degree of filling of 4.5%.
"IMPROVED" method for 100 µmol
solid support: HIGH-LOADED CPG 500 Å (MILLIPORE S.A., FRANCE)

capacity: 100 μmol/g
density: 3 ml/g
For 100 μmol: g of CPG that is to say 3 ml of phase and a degree of filling of 1.3%.
In comparison with the results described in Examples 1 to 4, the decrease in the duration of synthesis and the quantities of reagents is considerable. For the 100 μmol:
with the process according to the invention (Example 3 and Table 3), 118 ml of reagents and solvents are used and the duration of synthesis is 3 minutes per synthesis cycle;
with a MILLIPORE column, 500 ml of reagents and solvents are used, and the duration of synthesis is 20 minutes per cycle.

TABLE 1

| SOLVENTS OR REAGENTS | VESSEL NO. | VOLUME | IND. FLOW RATE | RATE | TOTAL FLOW TIME | |
|---|---|---|---|---|---|---|
| Dichloroethane, TFA 1% v/v | 10 | 20 ml | 72 ml/min | | 17 sec | |
| Waiting time | | | | | 20 sec | |
| Acetonitrile | 1 | 8 ml | 72 ml/min | | 7 sec | |
| 0.45M Tetrazole in acetonitrile | 2 | 3 ml | 60 ml/min | | 3 sec | |
| 0.45 Tetrazole in acetonitrile plus | 2 | 6 ml | 36 ml/min | | | |
| 0.1M monomer in acetonitrile | 3, 4, 5, 6 or 7 | 2 ml | 12 ml/min | | 48 ml/min | 10 sec |
| Waiting time | | | | | 20 sec | |
| 0.45M Tetrazole in acetonitrile | 2 | 1 ml | 60 ml/min | | 1 sec | |
| Acetonitrile | 1 | 2 ml | 60 ml/min | | 2 sec | |
| Iodine sat. with Acetic Acid plus | 8 | 2.5 ml | 30 ml/min | | 60 ml/min | 5 sec |
| Pyridine | 9 | 2.5 ml | 30 ml/min | | | |
| Acetonitrile | 1 | 10 ml | 60 ml/min | | 10 sec | |
| TOTAL | | 57 ml | | | 1 min 35 sec | |

TABLE 2

| SOLVENTS OR REAGENTS | VESSEL NO. | VOLUME | IND. FLOW RATE | RATE | TOTAL FLOW TIME | |
|---|---|---|---|---|---|---|
| Dichloroethane, TFA 1% v/v | 10 | 20 ml | 72 ml/min | | 17 sec | |
| Waiting time | | | | | 30 sec | |
| Acetonitrile | 1 | 8 ml | 72 ml/min | | 7 sec | |
| 0.45M Tetrazole in acetonitrile | 2 | 3 ml | 60 ml/min | | 3 sec | |
| 0.45 Tetrazole in acetonitrile plus | 2 | 6 ml | 36 ml/min | | 48.6 ml/min | 10 sec |
| 0.1M monomer in acetonitrile | 3, 4, 5, 6 or 7 | 2.1 ml | 12.6 ml/min | | | |
| Waiting time | | | | | 40 sec | |
| 0.45M Tetrazole in acetonitrile | 2 | 1 ml | 60 ml/min | | 1 sec | |
| Acetonitrile | 1 | 2 ml | 60 ml/min | | 2 sec | |
| Iodine sat. with Acetic Acid plus | 8 | 2.5 ml | 30 ml/min | | 60 ml/min | 5 sec |
| Pyridine | 9 | 2.5 ml | 30 ml/min | | | |
| Acetonitrile | 1 | 10 ml | 60 ml/min | | 10 sec | |
| TOTAL | | 57.1 ml | | | 2 min 05 sec | |

TABLE 3

| SOLVENTS OR REAGENTS | VESSEL NO. | VOLUME | IND. FLOW RATE | RATE | TOTAL FLOW TIME | |
|---|---|---|---|---|---|---|
| Dichloroethane, TFA 1% v/v | 10 | 40 ml | 84 ml/min | | 30 sec | |
| Waiting time | | | | | 30 sec | |
| Acetonitrile | 1 | 14 ml | 72 ml/min | | 15 sec | |
| 0.45M Tetrazole in acetonitrile | 2 | 6 ml | 60 ml/min | | 6 sec | |
| 0.45 Tetrazole in acetonitrile plus | 2 | 14 ml | 36 ml/min | | 48 ml/min | 25 sec |
| 0.1M monomer in acetonitrile | 3, 4, 5, 6 or 7 | 5 ml | 12 ml/min | | | |
| Waiting time | | | | | 45 sec | |
| 0.45M Tetrazole in acetonitrile | 2 | 3 ml | 60 ml/min | | 3 sec | |
| Acetonitrile | 1 | 6 ml | 60 ml/min | | 6 sec | |

TABLE 3-continued

| SOLVENTS OR REAGENTS | VESSEL NO. | VOLUME | IND. FLOW RATE | TOTAL FLOW TIME | |
|---|---|---|---|---|---|
| Iodine sat. with Acetic Acid plus | 8 | 5 ml | 30 ml/min | 60 ml/min | 10 sec |
| Pyridine | 9 | 5 ml | 30 ml/min | | |
| Acetonitrile | 1 | 20 ml | 60 ml/min | | 15 sec |
| TOTAL | | 118 ml | | | 3 min 05 sec |

TABLE 4

| STEP | | Dichloro-ethanel % v/v TFA Detritylation | Aceto-nitrile Wash 1 | 0.45M Tetrazole Coupling | 0.45M tetrazole 0.1M Monomers Coupling | 0.45M Tetrazole Wash 2 | Aceto-nitrile Wash 2 | Sol. of Iodine sat. Pyridine Oxidation | Aceto-nitrile Wash 3 | TOTAL VOLUME (ml) | TIME/CYCLE (min) |
|---|---|---|---|---|---|---|---|---|---|---|---|
| VESSEL NO. | | 10 | 1 | 2 | 3, 4, 5, 6 or 7 and 2 | 2 | 1 | 8 and 9 | 1 | | |
| 1 COLUMNS | VOLUME (ml) | 0.8 | 0.4 | 0.0375 | 0.08 | 0.025 | 0.4 | 0.1 | 0.4 | 2.2425 | |
| | FLOW RATE (ml/min) | 6 | 4.8 | 2.25 | 2.94 | 1.5 | 4.8 | 3 | 4.8 | | 0.48 |
| 2 COLUMNS | VOLUME (ml) | 1.2 | 0.6 | 0.075 | 0.16 | 0.05 | 0.6 | 0.15 | 0.6 | 3.435 | |
| | FLOW RATE (ml/min) | 9 | 7.2 | 4.5 | 2.94 | 3 | 7.2 | 3.15 | 7.2 | | 0.52 |
| 3 COLUMNS | VOLUME (ml) | 1.6 | 0.8 | 0.1125 | 0.24 | 0.075 | 0.8 | 0.2 | 0.8 | 4.6275 | |
| | FLOW RATE (ml/min) | 12 | 9.6 | 6.75 | 5.88 | 4.5 | 9.6 | 3.3 | 9.6 | | 0.52 |
| 4 COLUMNS | VOLUME (ml) | 2 | 1 | 0.15 | 0.32 | 0.1 | 1 | 0.25 | 1 | 5.82 | |
| | FLOW RATE (ml/min) | 15 | 12 | 9 | 8.82 | 6 | 12 | 3.45 | 12 | | 0.53 |
| 5 COLUMNS | VOLUME (ml) | 2.4 | 1.2 | 0.1875 | 0.4 | 0.125 | 1.2 | 0.3 | 1.2 | 7.0125 | |
| | FLOW RATE (ml/min) | 18 | 14.4 | 11.25 | 11.76 | 7.5 | 14.4 | 3.6 | 14.4 | | 0.53 |
| 6 COLUMNS | VOLUME (ml) | 2.8 | 1.4 | 0.225 | 0.48 | 0.15 | 1.4 | 0.35 | 1.4 | 8.205 | |
| | FLOW RATE (ml/min) | 21 | 16.8 | 13.5 | 14.7 | 9 | 16.8 | 3.75 | 16.8 | | 0.54 |
| 7 COLUMNS | VOLUME (ml) | 3.2 | 1.6 | 0.2625 | 0.56 | 0.175 | 1.6 | 0.4 | 1.6 | 9.3975 | |
| | FLOW RATE (ml/min) | 24 | 19.2 | 15.75 | 17.64 | 10.5 | 19.2 | 3.9 | 19.2 | | 0.55 |
| 8 COLUMNS | VOLUME (ml) | 3.6 | 1.8 | 0.3 | 0.64 | 0.2 | 1.8 | 0.45 | 1.8 | 10.59 | |
| | FLOW RATE (ml/min) | 27 | 21.6 | 18 | 20.58 | 12 | 21.6 | 4.05 | 21.6 | | 0.56 |
| 9 COLUMNS | VOLUME (ml) | 4 | 2 | 0.3375 | 0.72 | 0.225 | 2 | 0.5 | 2 | 11.7825 | |
| | FLOW RATE (ml/min) | 30 | 24 | 20.25 | 23.52 | 13.5 | 24 | 4.2 | 24 | | 0.56 |
| 10 COLUMNS | VOLUME (ml) | 4.4 | 2.2 | 0.375 | 0.8 | 0.25 | 2.2 | 0.55 | 2.2 | 12.975 | |
| | FLOW RATE (ml/min) | 33 | 26.4 | 22.5 | 26.46 | 15 | 26.4 | 4.35 | 26.4 | | 0.57 |
| 11 COLUMNS | VOLUME (ml) | 4.8 | 2.4 | 0.4125 | 0.88 | 0.275 | 2.4 | 0.6 | 2.4 | 14.1675 | |
| | FLOW RATE (ml/min) | 36 | 28.8 | 24.75 | 29.4 | 16.5 | 28.8 | 4.5 | 28.8 | | 0.58 |
| 12 COLUMNS | VOLUME (ml) | 5.2 | 2.6 | 0.45 | 0.96 | 0.3 | 2.6 | 0.65 | 2.6 | 15.36 | |
| | FLOW RATE (ml/min) | 39 | 31.2 | 27 | 32.34 | 18 | 31.2 | 4.65 | 31.2 | | 0.59 |
| 13 COLUMNS | VOLUME (ml) | 5.6 | 2.8 | 0.4875 | 1.04 | 0.325 | 2.8 | 0.7 | 2.8 | 16.5525 | |
| | FLOW RATE (ml/min) | 42 | 33.6 | 29.25 | 35.28 | 19.5 | 33.6 | 4.8 | 33.6 | | 0.59 |
| 14 COLUMNS | VOLUME (ml) | 6 | 3 | 0.525 | 1.12 | 0.35 | 3 | 0.75 | 3 | 17.745 | |
| | FLOW RATE (ml/min) | 45 | 36 | 31.5 | 38.22 | 21 | 36 | 4.95 | 36 | | 0.60 |
| 15 | VOLUME | 6.4 | 3.2 | 0.5625 | 1.2 | 0.375 | 3.2 | 0.8 | 3.2 | 18.9375 | |

TABLE 4-continued

| STEP | | Dichloro-ethanel % v/v TFA Detritylation | Aceto-nitrile Wash 1 | 0.45M Tetrazole Coupling | 0.45M tetrazole 0.1M Monomers Coupling | 0.45M Tetrazole Wash 2 | Aceto-nitrile Wash 2 | Sol. of Iodine sat. Pyridine Oxidation | Aceto-nitrile Wash 3 | TOTAL VOLUME (ml) | TIME/ CYCLE (min) |
|---|---|---|---|---|---|---|---|---|---|---|---|
| COLUMNS | (ml) | | | | | | | | | | |
| | FLOW RATE (ml/min) | 48 | 38.4 | 33.75 | 41.16 | 22.5 | 38.4 | 5.1 | 38.4 | | 0.60 |
| 16 COLUMNS | VOLUME (ml) | 6.8 | 3.4 | 0.6 | 1.28 | 0.4 | 3.4 | 0.85 | 3.4 | 20.13 | |
| | FLOW RATE (ml/min) | 51 | 40.8 | 36 | 44.1 | 24 | 40.8 | 5.25 | 40.8 | | 0.61 |
| 17 COLUMNS | VOLUME (ml) | 7.2 | 3.6 | 0.6375 | 1.36 | 0.425 | 3.6 | 0.9 | 3.6 | 21.3225 | |
| | FLOW RATE (ml/min) | 54 | 43.2 | 38.25 | 47.04 | 25.5 | 43.2 | 5.4 | 43.2 | | 0.61 |
| 18 COLUMNS | VOLUME (ml) | 7.6 | 3.8 | 0.675 | 1.44 | 0.45 | 3.8 | 0.95 | 3.8 | 22.515 | |
| | FLOW RATE (ml/min) | 57 | 45.6 | 40.5 | 49.98 | 27 | 45.6 | 5.55 | 45.6 | | 0.62 |
| 19 COLUMNS | VOLUME (ml) | 8 | 4 | 0.7125 | 1.52 | 0.475 | 4 | 1 | 4 | 23.7075 | |
| | FLOW RATE (ml/min) | 60 | 48 | 42.75 | 52.92 | 28.5 | 48 | 5.7 | 48 | | 0.62 |
| 20 COLUMNS | VOLUME (ml) | 8.4 | 4.2 | 0.75 | 1.6 | 0.5 | 4.2 | 1.05 | 4.2 | 24.9 | |
| | FLOW RATE (ml/min) | 63 | 50.4 | 45 | 55.86 | 30 | 50.4 | 5.85 | 50.4 | | 0.62 |
| 21 COLUMNS | VOLUME (ml) | 8.8 | 4.4 | 0.7875 | 1.68 | 0.525 | 4.4 | 1.1 | 4.4 | 26.0925 | |
| | FLOW RATE (ml/min) | 66 | 52.8 | 47.25 | 58.8 | 31.5 | 52.8 | 6 | 52.8 | | 0.63 |
| 22 COLUMNS | VOLUME (ml) | 9.2 | 4.6 | 0.825 | 1.76 | 0.55 | 4.6 | 1.15 | 4.6 | 27.285 | |
| | FLOW RATE (ml/min) | 69 | 55.2 | 49.5 | 61.74 | 33 | 55.2 | 6.15 | 55.2 | | 0.63 |
| 23 COLUMNS | VOLUME (ml) | 9.6 | 4.8 | 0.8625 | 1.84 | 0.575 | 4.8 | 1.2 | 4.8 | 28.4775 | |
| | FLOW RATE (ml/min) | 72 | 57.6 | 51.75 | 64.68 | 34.5 | 57.6 | 6.3 | 57.6 | | 0.64 |
| 24 COLUMNS | VOLUME (ml) | 10 | 5 | 0.9 | 1.92 | 0.6 | 5 | 1.25 | 5 | 29.67 | |
| | FLOW RATE (ml/min) | 75 | 60 | 54 | 67.62 | 36 | 60 | 6.45 | 60 | | |

TABLE 5

| COLUMN NO. | OLIGO | 5' Trityl | No bases | 5'–3' SEQUENCE |
|---|---|---|---|---|
| 0 | OLIGO1 | YES | 12 | TTT TTT TTT TTT |
| 1 | OLIG02 | NO | 12 | TTT TTT TTT TTT |
| 2 | OLIG03 | YES | 15 | TTT TTT TTT TTT TTT |
| 3 | OLIG04 | NO | 15 | TTT TTT TTT TTT TTT |
| 4 | OLIG05 | YES | 18 | TTT TTT TTT TTT TTT TTT |
| 5 | OLIG06 | NO | 18 | TTT TTT TTT TTT TTT TTT |
| 6 | OLIG07 | YES | 12 | AAA AAA AAA AAA |
| 7 | OLIG08 | NO | 12 | AAA AAA AAA AAA |
| 8 | OLIG09 | YES | 15 | AAA AAA AAA AAA AAA |
| 9 | OLIGO10 | NO | 15 | AAA AAA AAA AAA AAA |
| 10 | OLIGO11 | YES | 18 | AAA AAA AAA AAA AAA AAA |
| 11 | OLIG012 | NO | 18 | AAA AAA AAA AAA AAA AAA |
| 12 | OLIG013 | YES | 12 | CCC CCC CCC CCC |
| 13 | OLIG014 | NO | 12 | CCC CCC CCC CCC |
| 14 | OLIG015 | YES | 15 | CCC CCC CCC CCC CCC |
| 15 | OLIG016 | NO | 15 | CCC CCC CCC CCC CCC |
| 16 | OLIG017 | YES | 18 | CCC CCC CCC CCC CCC CCC |
| 17 | OLIG018 | NO | 18 | CCC CCC CCC CCC CCC CCC |
| 18 | OLIG019 | YES | 12 | AGT CAG TCA GTC |
| 19 | OLIG020 | NO | 12 | AGT CAG TCA GTC |
| 20 | OLIG021 | YES | 15 | AGT CAG TCA GTC AGT |
| 21 | OLIG022 | NO | 15 | AGT CAG TCA GTC AGT |
| 22 | OLIG023 | YES | 18 | AGT CAG TCA GTC AGT CAG |
| 23 | OLIG024 | NO | 18 | AGT CAG TCA GTC AGT CAG |

TABLE 6

| SYNTHESIZERS CHARACTERISTICS SYNTHESIS SCALE METHOD | ABI 394 4 COLUMNS 0.2 μmol STANDARD* | MILLIPORE LARGE-SCALE 100 μmol STANDARD** | MILLIPORE LARGE-SCALE 100 μmol IMPROVED** |
|---|---|---|---|
| REAGENTS | (ml) | (ml) | (ml) |
| MONOMERS 0.1M | 0.110 | 5 | 2.62 |
| TETRAZOLE SOLUTION | 0.400 | 20.3 | 19 |
| CAP A (acetic anhydride) | 0.290 | 9 | 6.25 |
| CAP B (N-methylimidazole) | 0.260 | 11.6 | 8.65 |
| DEBLOCK (TCA/DCM) | 1.100 | 84.3 | 68.75 |
| IODINE SOLUTION | 0.350 | 40 | 33 |
| ACETONITRILE | 8.000 | 376 | 286.25 |
| TOTAL | 10,510 | 546.2 | 424.52 |
| TIME PER CYCLE | 6 min | 20 min | 22 min |

*APPLIED BIOSYSTEMS
Instruction manual for the ABI 394 synthesizer
**N.D. SINHA, S. FRY; 3rd CAMBRIDGE SYMPOSIUM
Oligonucleotides & Analogues, 5–8 Sep. 1992
POSTER COMMUNICATION

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
       (A) NAME/KEY: CDS
       (B) LOCATION: 1..18

(xi) SEQUENCE DESCRIPTION: SEQ ID NO: 1:

ACG TTC CTC CTG CGG GAA                                        18
Thr Phe Leu Leu Arg Glu
 1               5

(2) INFORMATION FOR SEQ ID NO: 2:

(i) SEQUENCE CHARACTERISTICS:
       (A) LENGTH: 6 amino acids
       (B) TYPE: amino acid
       (D) TOPOLOGY: linear (ii) MOLECULE TYPE: protein (xi) SEQUENCE DESCRIPTION: SEQ ID NO: 2:

Thr Phe Leu Leu Arg Glu
 1               5

(2) INFORMATION FOR SEQ ID NO: 3:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
       (A) NAME/KEY: CDS
       (B) LOCATION: 1..18

(xi) SEQUENCE DESCRIPTION: SEQ ID NO: 3:

TTC CGC CAG GAG GAA CGT                                        18
Phe Arg Gln Glu Glu Arg
 1               5

(2) INFORMATION FOR SEQ ID NO: 4:

(i) SEQUENCE CHARACTERISTICS:
         (A) LENGTH: 6 amino acids
         (B) TYPE: amino acid
         (D) TOPOLOGY: linear (ii) MOLECULE TYPE: protein (xi) SEQUENCE DESCRIPTION: SEQ ID NO: 4:

Phe Arg Gln Glu Glu Arg
 1               5

(2) INFORMATION FOR SEQ ID NO: 5:

(i) SEQUENCE CHARACTERISTICS:
         (A) LENGTH: 56 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
         (A) NAME/KEY: CDS
         (B) LOCATION: 1..56

(xi) SEQUENCE DESCRIPTION: SEQ ID NO: 5:

TAA CCA CAC TTT TTG TGT GGT TAA TGA TCT ACA GTT ATT TTT TAA CTG       48
 *  Pro His Phe Leu Cys Gly  *   *  Ser Thr Val Ile Phe  *  Leu 1              5                  10                 15

TAG ATC AT                                                            56
 *  Ile (2) INFORMATION FOR SEQ ID NO: 6:

(i) SEQUENCE CHARACTERISTICS:
         (A) LENGTH: 6 amino acids
         (B) TYPE: amino acid
         (D) TOPOLOGY: linear (ii) MOLECULE TYPE: protein (xi) SEQUENCE DESCRIPTION: SEQ ID NO: 6:

Pro His Phe Leu Cys Gly
 1               5

(2) INFORMATION FOR SEQ ID NO: 7:

(i) SEQUENCE CHARACTERISTICS:
         (A) LENGTH: 5 amino acids
         (B) TYPE: amino acid
         (D) TOPOLOGY: linear (ii) MOLECULE TYPE: protein (xi) SEQUENCE DESCRIPTION: SEQ ID NO: 7:

Ser Thr Val Ile Phe
 1               5

(2) INFORMATION FOR SEQ ID NO: 8:

(i) SEQUENCE CHARACTERISTICS:
         (A) LENGTH: 12 base pairs
         (B) TYPE: nucleic acid (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
            (A) NAME/KEY: CDS
            (B) LOCATION: 1..12

(xi) SEQUENCE DESCRIPTION: SEQ ID NO: 8:

```
TTT TTT TTT TTT                                                        12
Phe Phe Phe Phe
  1
```

(2) INFORMATION FOR SEQ ID NO: 9:

(i) SEQUENCE CHARACTERISTICS:
            (A) LENGTH: 4 amino acids
            (B) TYPE: amino acid
            (D) TOPOLOGY: linear (ii) MOLECULE TYPE: protein (xi) SEQUENCE DESCRIPTION: SEQ ID NO: 9:

```
Phe Phe Phe Phe
  1
```

(2) INFORMATION FOR SEQ ID NO: 10:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
            (A) NAME/KEY: CDS
            (B) LOCATION: 1..15

(xi) SEQUENCE DESCRIPTION: SEQ ID NO: 10:

```
TTT TTT TTT TTT TTT                                                    15
Phe Phe Phe Phe Phe
  1               5
```

(2) INFORMATION FOR SEQ ID NO: 11:

(i) SEQUENCE CHARACTERISTICS:
            (A) LENGTH: 5 amino acids
            (B) TYPE: amino acid
            (D) TOPOLOGY: linear (ii) MOLECULE TYPE: protein (xi) SEQUENCE DESCRIPTION: SEQ ID NO: 11:

```
Phe Phe Phe Phe Phe
  1               5
```

(2) INFORMATION FOR SEQ ID NO: 12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 1..18

(xi) SEQUENCE DESCRIPTION: SEQ ID NO: 12:

```
TTT TTT TTT TTT TTT TTT                                              18
Phe Phe Phe Phe Phe Phe
 1               5
```

(2) INFORMATION FOR SEQ ID NO: 13:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 13:

```
Phe Phe Phe Phe Phe Phe
 1               5
```

(2) INFORMATION FOR SEQ ID NO: 14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 1..12

(xi) SEQUENCE DESCRIPTION: SEQ ID NO: 14:

```
AAA AAA AAA AAA                                                      12
Lys Lys Lys Lys
 1
```

(2) INFORMATION FOR SEQ ID NO: 15:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 15:

Lys Lys Lys Lys
 1

(2) INFORMATION FOR SEQ ID NO: 16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 1..15

(xi) SEQUENCE DESCRIPTION: SEQ ID NO: 16:

AAA AAA AAA AAA AAA                                                        15
Lys Lys Lys Lys Lys
 1               5

(2) INFORMATION FOR SEQ ID NO: 17:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 17:

Lys Lys Lys Lys Lys
 1               5

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 1..18

(xi) SEQUENCE DESCRIPTION: SEQ ID NO: 18:

AAA AAA AAA AAA AAA AAA                                                    18
Lys Lys Lys Lys Lys Lys
 1               5

(2) INFORMATION FOR SEQ ID NO: 19:

(i) SEQUENCE CHARACTERISTICS:
        (A) LENGTH: 6 amino acids
        (B) TYPE: amino acid

```
            (D) TOPOLOGY: linear (ii) MOLECULE TYPE: protein (xi) SEQUENCE DESCRIPTION: SEQ ID NO: 19:

Lys Lys Lys Lys Lys Lys
 1               5

(2) INFORMATION FOR SEQ ID NO: 20:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
         (A) NAME/KEY: CDS
         (B) LOCATION: 1..12

(xi) SEQUENCE DESCRIPTION: SEQ ID NO: 20:

CCC CCC CCC CCC                                                           12
Pro Pro Pro Pro
 1

(2) INFORMATION FOR SEQ ID NO: 21:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 21:

Pro Pro Pro Pro
 1

(2) INFORMATION FOR SEQ ID NO: 22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
         (A) NAME/KEY: CDS
         (B) LOCATION: 1..15

(xi) SEQUENCE DESCRIPTION: SEQ ID NO: 22:

CCC CCC CCC CCC CCC                                                       15
Pro Pro Pro Pro Pro
 1               5
```

```
(2) INFORMATION FOR SEQ ID NO: 23:

(i) SEQUENCE CHARACTERISTICS:
          (A) LENGTH: 5 amino acids
          (B) TYPE: amino acid
          (D) TOPOLOGY: linear (ii) MOLECULE TYPE: protein (xi) SEQUENCE DESCRIPTION: SEQ ID NO: 23:

Pro Pro Pro Pro Pro
  1               5

(2) INFORMATION FOR SEQ ID NO: 24:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
          (A) NAME/KEY: CDS
          (B) LOCATION: 1..18

(xi) SEQUENCE DESCRIPTION: SEQ ID NO: 24:

CCC CCC CCC CCC CCC CCC                                              18
Pro Pro Pro Pro Pro Pro
  1               5

(2) INFORMATION FOR SEQ ID NO: 25:

(i) SEQUENCE CHARACTERISTICS:
          (A) LENGTH: 6 amino acids
          (B) TYPE: amino acid
          (D) TOPOLOGY: linear (ii) MOLECULE TYPE: protein (xi) SEQUENCE DESCRIPTION: SEQ ID NO: 25:

Pro Pro Pro Pro Pro Pro
  1               5

(2) INFORMATION FOR SEQ ID NO: 26:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
          (A) NAME/KEY: CDS
          (B) LOCATION: 1..12

(xi) SEQUENCE DESCRIPTION: SEQ ID NO: 26:
```

```
AGT CAG TCA GTC                                                    12
Ser Gln Ser Val
  1
```

(2) INFORMATION FOR SEQ ID NO: 27:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 27:

```
Ser Gln Ser Val
  1
```

(2) INFORMATION FOR SEQ ID NO: 28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 1..15

(xi) SEQUENCE DESCRIPTION: SEQ ID NO: 28:

```
AGT CAG TCA GTC AGT                                                15
Ser Gln Ser Val Ser
  1               5
```

(2) INFORMATION FOR SEQ ID NO: 29:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 29:

```
Ser Gln Ser Val Ser
  1               5
```

(2) INFORMATION FOR SEQ ID NO: 30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:

-continued

```
        (A) NAME/KEY: CDS
        (B) LOCATION: 1..18

(xi) SEQUENCE DESCRIPTION: SEQ ID NO: 30:

AGT CAG TCA GTC AGT CAG                                          18
Ser Gln Ser Val Ser Gln
  1               5

(2) INFORMATION FOR SEQ ID NO: 31:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 31:

Ser Gln Ser Val Ser Gln
  1               5
```

What is clamied is:

1. An anhydrous oxidizing iodine-containing composition for use in oligonucleotide synthesis comprising a combination of iodine dissolved in glacial acetic acid as first component and pyridine as second component.

2. The composition of claim 1 wherein the first component consists of a saturated solution of iodine in glacial acetic acid.

3. The composition of claim 1 wherein the ratios of the volumes of the two components equals 1.

* * * * *